United States Patent [19]

Denton et al.

[11] 4,293,220

[45] Oct. 6, 1981

[54] APPLICATION OF INDUCTIVELY COUPLED PLASMA EMISSION SPECTROMETRY TO THE ELEMENTAL ANALYSIS OF ORGANIC COMPOUNDS AND TO THE DETERMINATION OF THE EMPIRICAL FORMULAS FOR THESE AND OTHER COMPOUNDS

[75] Inventors: Medona B. Denton, Tucson, Ariz.; David L. Windsor, Cincinnati, Ohio

[73] Assignee: The United States of America as represented by the Secretary of the Navy, Washington, D.C.

[21] Appl. No.: 53,664

[22] Filed: Jul. 2, 1979

[51] Int. Cl.³ ............................................. G01N 21/73
[52] U.S. Cl. ................................................. 356/316
[58] Field of Search ................................ 356/316, 328

[56] References Cited
U.S. PATENT DOCUMENTS

| | | | |
|---|---|---|---|
| 3,521,959 | 7/1970 | Fassel et al. | 356/316 |
| 3,874,799 | 4/1975 | Isaacs et al. | 250/228 |
| 3,887,280 | 6/1975 | McLean | 356/316 |
| 3,958,883 | 5/1976 | Turner | 356/316 |
| 4,140,394 | 2/1979 | Roos | 356/328 |

Primary Examiner—Vincent P. McGraw
Attorney, Agent, or Firm—Richard S. Sciascia; Thomas M. Phillips

[57] ABSTRACT

An inductively coupled plasma torch (ICP) provides an efficient means for thermally degrading many organic molecules and exciting the resulting atomic species into optical emission. Spectrometric analysis produces reliable data for qualitative and quantiative simultaneous, multi-element analyses. To determine the empirical formula of a molecular compound, a gas chronometer is used to separate a mixture and atomic emission monitored continuously by a multi-channel spectrometer over the period of time required for the rise and fall of the elution. The plural channels provide parallel outputs defining intensity relationships or ratios of the excited elements. Instantaneous sampling repetitively made during the elution period provides a large number of discrete ratios that are averaged to provide the desired empirical formula. Molecular formulas then are derivable.

3 Claims, 3 Drawing Figures

APPLICATION OF INDUCTIVELY COUPLED PLASMA EMISSION SPECTROMETRY TO THE ELEMENTAL ANALYSIS OF ORGANIC COMPOUNDS AND TO THE DETERMINATION OF THE EMPIRICAL FORMULAS FOR THESE AND OTHER COMPOUNDS

BACKGROUND OF THE INVENTION

The present invention relates to procedures for analyzing the multi-element atomic composition of molecular compounds and, in particular, to the use of inductively coupled plasma torch optical emission spectrometry (ICP-OES) for this purpose.

As may be known, ICP arrangements usually employ an RF transmitter supplying power to a load coil wound on the torch to energize a plasma or auxiliary gas, such as argon. The energy produces a high temperature plasma environment into which a sample mixed with a carrier gas is introduced. Coolant argon also is used. The high temperature environment thermally degrades the molecular sample and the resulting atomic species are excited to produce radiation emissions detected by optical spectrometric procedures.

In the past, another commonly-used procedure has been the familiar flame photometry from which, in fact, the present ICP procedure essentially is an outgrowth or extension. Also, important analytical work has been conducted with the use of the so-called microwave-excited plasmas (MEPs). However, for one reason or another, these procedures are found to be somewhat limited in their applications. In particular, problems arise when they are applied to the elemental analyses of organic compounds. Flame photometry, for example, is fundamentally inconsistent with organic compound evaluations since the hydrogen in organics also is present in the gas normally used to support the flame.

With regard to MEP, it is recognized that a number of investigators have reported its use for the elemental analysis of organic compounds. However, certain problems have been noted. For example, the emission intensity of an element often is found to be dependent on the structure of the organic molecular compound and the wavelength of maximum intensity for a given element is not consistently the same for all compounds containing that element. Also, there is a problem regarding the recombination of atoms to form diatomic species which, in fact, occurs to such an extent that molecular band heads sometimes are employed for analysis in several MEP systems. A further difficulty is that carbon-, sulfur-, and phosphorus-containing compounds form deposits on the quartz excitation cells of the MEP. In fact, the dependence of carbon response per unit weight on the carbon number of the compound has been attributed to the formation of carbon deposits inside the MEP cell. Molecular oxygen or nitrogen added to the microwave support gas has helped reduce these formations.

In some contrast to the use of MEP, relatively little work has been reported on the use of ICP-OES for the analysis of elements in organic compounds. In particular, Fassel, et al have determined wear metals in oils, (Ref. 1, V. A. Fassel, et al, Anal. Chem. 48,516 (1976). Ward reports the determination of metals in organic solvents (Ref. 2, A. F. Ward, ICP Information Newsletter 1, 266 (1976). Nishimura studied the decomposition of gaseous hydrocarbons but was unable to maintain a stable plasma when the organic sample is introduced in a conventional manner (Ref. 3, Y. Nishimura, ICP Information Newsletter 1, 126 (1975). Greenfield and Smith analyzed blood plasma for phosphorus and silicon (Ref. 4, S. Greenfield, et al, Anal. Chim. Acta 59, 341 (1972), and Kniseley, et al determined phosphorus along with several metallic elements in whole blood (Ref. 5, R. N. Kniseley, et al, Clin. Chem. 19,807 (1973). Several non-metallic elements present in organic compounds also have been determined by ICP-OES as inorganic ions in aqueous solutions and a detection limit of 0.1 ppm for phosphorus in diluted oils has been reported (Ref. 6, F. Breach, ICP Information Newsletter 1, 171 (1976) from a Jarrell-Ash Application Note). In summary, these reports, as well as others, are of considerable interest in that they indicate the applicability of ICP-EOS to the multi-element detection of a rather wide variety of elements. However, as far as is known, this technique has not been successfully used for the elemental analysis of organic compounds which is one of the major objects of the present invention. Another very important object is to utilize the ICP to determine the actual empirical formula of an organic compound or other similar compounds. Again, the prior art apparently has not considered this particular aspect even though its achievement should be of considerable benefit.

STATEMENT OF THE INVENTION

The present invention establishes the applicability of ICP/OES to the elemental analysis of organic compounds. The procedure is shown to be sensitive and relatively free from interference and reasonably independent of molecular structure for a wide variety of compounds. In particular, ICP/OES is found to be capable of detecting multi-elements of organic compounds simultaneously and this capability is used to determine the empirical and molecular formulas of organic and other compounds. For empirical formula determinations, a gas chromatograph supplies the sample to an ICP monitored by a multi-channel spectrometer having a parallel ratiometric output which can be averaged in a computer to provide the formula.

BRIEF DESCRIPTION OF THE DRAWINGS

The present invention is illustrated in the accompanying drawings of which.

DETAILED DESCRIPTION OF THE INVENTION

The present invention essentially is the result of an experimental evaluation the primary purpose of which has been to determine the applicability of ICP-OES to the elemental analysis of organic compounds. As will be shown, the resulting data clearly demonstrates the desired capability and, further, has extended the effort to the determination of empirical and molecular formulas for the compounds. In the present description, the results of the basic capability study first will be considered. Subsequently, the extension of the study to empirical formula determination will be described.

INSTRUMENTATION

Figure 1:
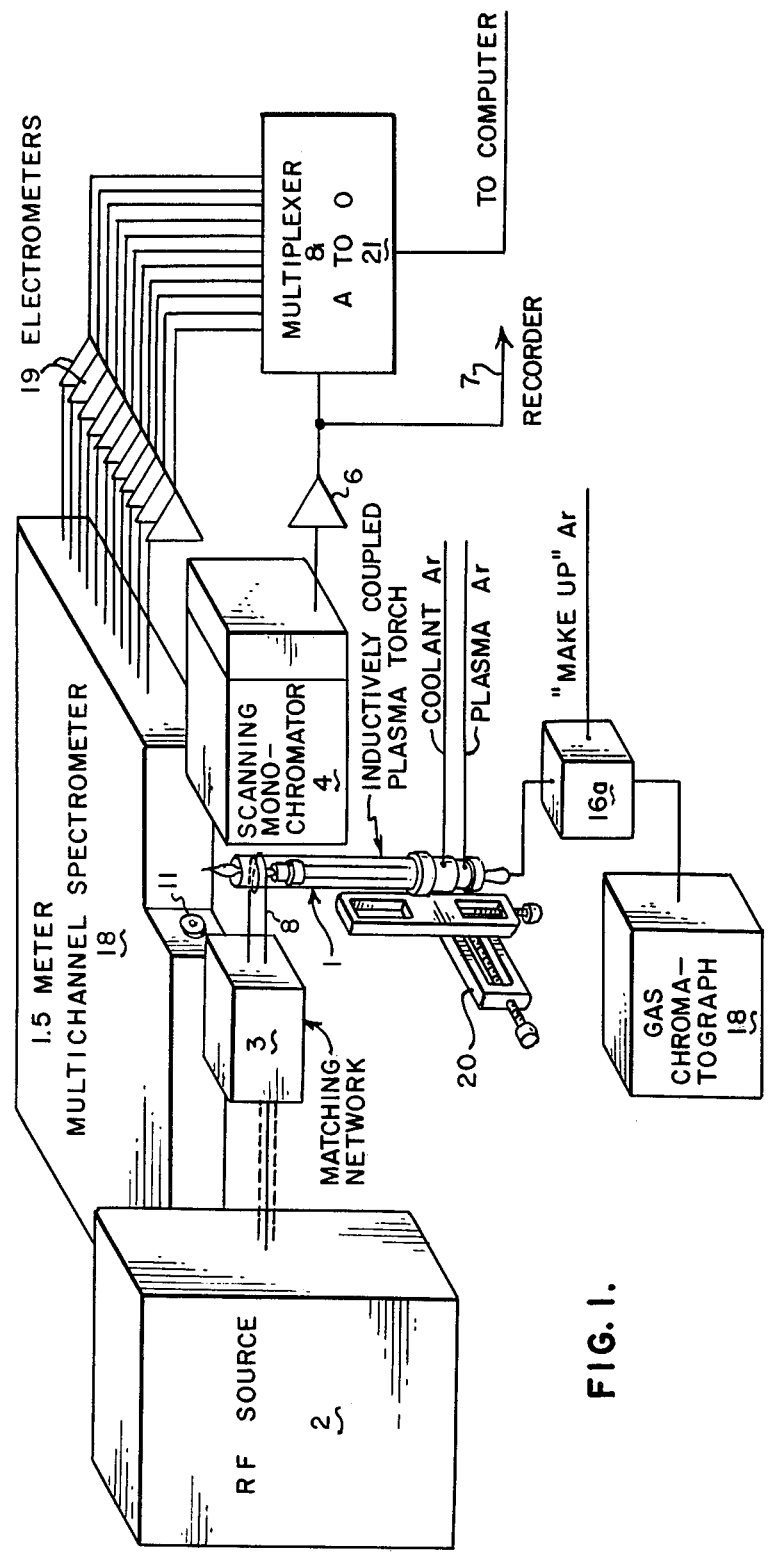
FIG. 1 is a block diagram of the system.

The instrumentation for the study is shown in the block diagram of FIG. 1. However, in the initial experiments, the components included only the use of an inductively coupled plasma torch 1, a radio frequency (RF) source 2, a matching network 3, a scanning monochromator 4, an FET input electrometer 6 and a suitable strip chart recorder the presence of which is indicated by arrow 7. Other components shown in FIG. 1 were used subsequently for simultaneous multi-element detection purposes and they will be described in conjunction with the descriptions of those studies.

Figure 3:
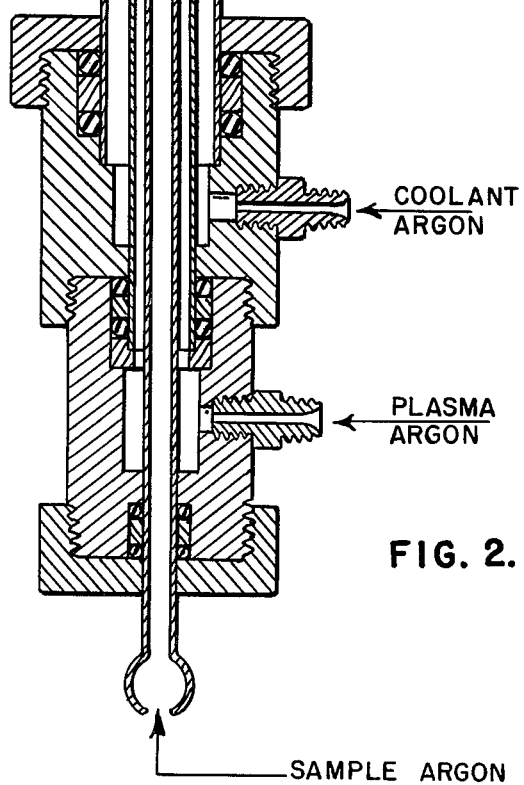
FIG. 3 is a diagram showing an impedance matching network used to couple RF power to the torch.

With regard to the identified components, the RF power is provided by a Collins radio AN/FRT-24 (Cedar Rapids, Iowa) transmitter having a frequency variable from 2 to 30 MHz and power to 1 kilowatt. The 52 ohm output impedance of the transmitter is matched to the low impedance of the load coil by a capacitive network similar to that shown in FIG. 3. A load coil 8, for the torch, is two turns of 5 mm o.d. copper tubing having a mean diameter of 27 mm with a spacing between turns of 1 mm. Both the matching network connections and the load coil are water cooled.

Plasma torch 1 is a specially constructed torch described and claimed in a co-pending patent application, Ser. No. 54,048 filed in the names of Medona B. Denton, David L. Windsor and David R. Heine entitled "A High-Power Dismountable and Self-Aligning Inductively-Coupled Plasma Torch". Other conventional torch arrangements, having a characteristically long residence time (~2 ms) in a relatively high temperature plasma environment (5000° K. or more), can be used.

Figure 2:
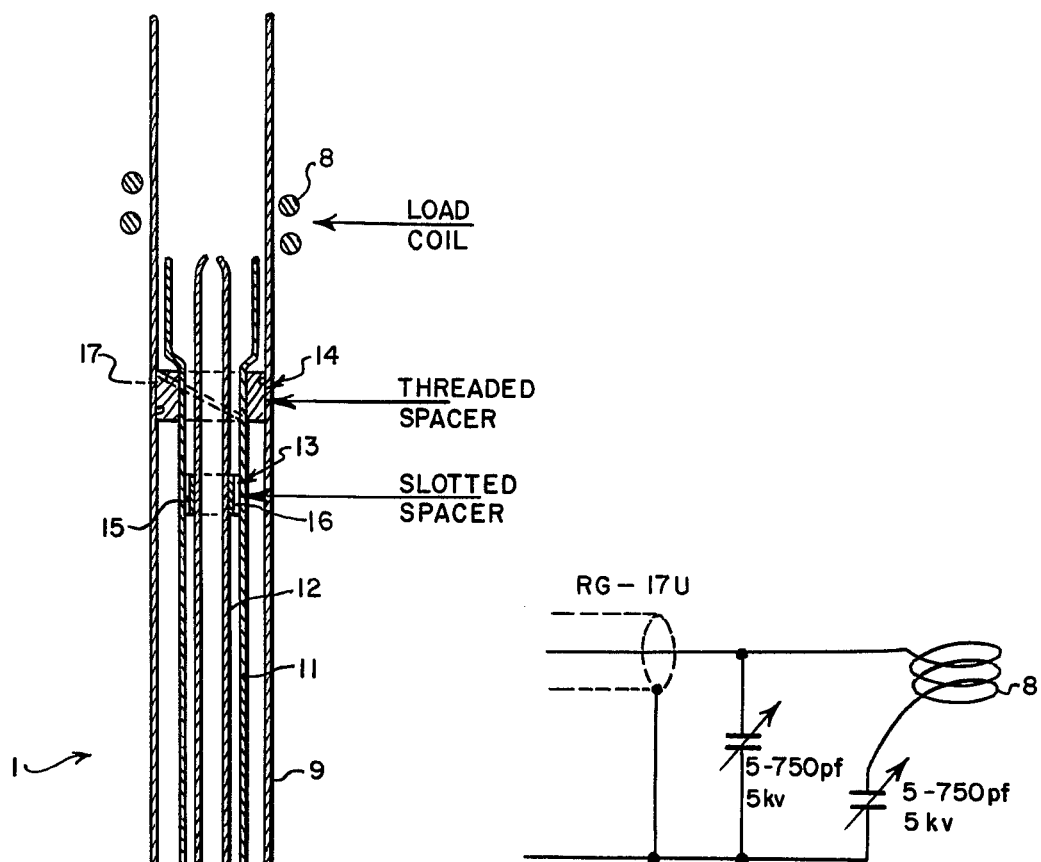
FIG. 2 is a somewhat schematic sectional view of a particular inductively coupled plasma torch used in the system.

As shown in FIG. 2, torch 1 is a concentric arrangement including an outer coolant tube 9, a middle plasma tube 11 and an inner sample tube 12. The coolant and plasma tubes may be quartz and the sample tube Pyrex. The center of load coil 8 is positioned 10 mm above the top of the sample tube 12 and the coolant tube extends 5 cm above the top of the load coil. Such a concentric arrangement, as will be recognized, is conventional although other features are not. In particular, these other features principally involve the use of nylon spacer rings 13 and 14 fitted between the concentric ring. One purpose of the rings is to maintain concentricity while, nevertheless, permitting the torch to be dismantled for repair, etc. However, it also will be noted that the spacer rings each are provided with special slots or channels 15 and 16. Thus, ring 13 has a series of peripheral slots 15 directing the flow in a manner that improves its laminar flow. Similarly, spacer ring 14 has peripheral threads 16 providing spiral passageways to increase the tangential velocity of the coolant gas. Together, the slotted ring arrangements significantly improve the flow characteristics to stablize the plasma discharge and, in particular, improve the heat transfer capability of the coolant. Higher operating temperatures and longer coolant tubes thus can be used to promote complete degradation of the molecular compound into its atomic species.

The compound or sample to be analyzed is introduced into the lower end of the sample tube 12 along with a inert gas such as argon, conventionally used as a carrier gas. Plasma argon, concurrently, is supplied through tube 11 and coolant argon through tube 9. The sample, of course, is introduced directly into the high temperature environment of the plasma where it is excited into radiative emission that is monitored by scanning monochrometer 4. The monochrometer can be a model EU-700 GCA McPherson (Acton, MA) having a single pass Czerny-Turner mounting with an 1180 line/mm grating blazed at 2500 Å focal length 350 mm. To control the monochrometer wavelength Heath (benton Harbor, MS) Model EU-700-51 wavelength drive can be used. Radiation is detected with a Heath Model EU-701-30 photo multiplier module equipped with either an RCA (Harrison, NJ) 1P28A or a Hamamatsu (Middlesex, NJ) R212/UN photo multiplier tube. Output is amplified by FET input electrometer 6 and the signal recorded either on a Heath Model EU 20-DB strip chart recorder or a Spectra Physics (Santa Clara, Calif.) Auto Lab I computing integrator. A 2.54 cm diameter 23.5 mm focal length (at 2500 Å) quartz lens used between the plasma torch and the monochrometer entrance slit the lens is positioned so that a 5 mm horizontal section from the center of the plasma is focused on the entrance slit of the monochrometer. Matching network 3 and plasma torch 1 both are mounted on a motor-drive Velmex Model 2509B (Bloomfield, NY) slide arrangement 10 allowing the horizontal and vertical position of the plasma torch to be varied.

A single argon tank with a Matheson Model 18-580 dual diaphragm regulator can be used to supply the argon for the torch. All argon flow rates are controlled by conventional needle valves which can be monitored with rotometers. In the experiments, a P-5 gas (Matheson, 5.0% methane, 95.0% argon) was employed, this reagent being AR grade without further purification. The P-5 gas was used initially as a sample for determining the effect of the coolant at sample argon flow rates on the atomic carbon emission. It also was used to optimize the carbon response with respect to position in the plasma. The maximum flow rate of methane into the sample gas stream at which a stable plasma could be maintained was 0.25 ml/min or 0.01 g/s.

To obtain the spectra of the organic compounds, the sample gas stream passes continuously over an organic liquid with sufficient vapor pressure to produce a detectable spectra. Plasma cannot be easily initiated if an excessive quantity of organic species is present in the sample stream. Consequently, the stream is split with only a small fraction flowing over the organic compound. The organic compound and mixtures used in the detection limit and interference studies to be described, can be introduced into the sample gas stream via a heated injection block and the flow splitter. Such an injection block is commonly used to vaporize the sample. A splitting of 1:20 with a entering flow rate of 1.0 liter/minute was employed. This results in an exit flow rate of 0.05 liter/minute which is increased to 0.9 liter/minute by the addition of "make-up" argon before entering the sample tube of the plasma torch. Detection limits and dynamic ranges can be determined using the conditions shown in Table I and the solutions of organic compounds given in Table II.

TABLE I

| Operating parameters. | |
|---|---|
| Frequency | 27 MHz |
| Power | ~800 W |
| Flow rates | |
| Coolant Ar | 12 liters/min |
| Sample Ar | 0.9 liter/min |
| Plasma Ar | 0.3 liter/min |
| "Make up" Ar | 1.0 liter/min |
| Vertical position | 9 mm |
| Slit width | 100 μm |

TABLE I-continued

| Operating parameters. | |
|---|---|
| Injection port temperature | 200 °C. |

TABLE II

| Solutions for determining detection limits and dynamic ranges. | | |
|---|---|---|
| Element | Compound | Solvent |
| B | Tri-n-butylborate | DMSO |
| C | Acetone | Water |
| H | η-Heptane | CCl$_4$ |
| I | Ethyl iodide | DMSO |
| P | Diethylphosphite | DMSO |
| S | Thiophene | Benzene |
| Si | Tetravinylsilane | Benzene |

The compounds listed in column 2 of Table II were used to determine vertical emission profiles of the elements with the exception that n-Heptane was used for carbon. Pure carbons were employed for the determination of carbon response factors.

A condensing lens was used in all further studies. In all cases the monochromator was set at the analysis line and 0.5 μm samples were injected into the injection port with a 10 μl syringe. The total sample entering the plasma was 0.025 μl due to the 1:20 splitting ratio. For the majority of organic compounds, the response appeared as a very narrow (~0.1 s) peaks when the response was recorded on a strip chart recorder. The height of these peaks was taken as a measure of the response for the vertical position profiles and detection limits. Integrated peak areas were used as a measure of the response in the carbon response factor studies in order to include those compounds which produced broad peaks with the present sampling system. Background measurements were made by repeating this procedure at wavelengths approximately 5 Å above and below the analysis line.

Other factors pertinent to the experimental evaluation and to the results that it has produced also should be noted. Thus, with regard to the various flow rates, the observed effect of the coolant argon flow rate on the atomic emission intensities is similar to that previously reported by Kirkbright, et al (Ref. 7, Anal. Chim. Acta 62, 241 (1972). Up to 14 liters/min, the emission intensity decreases slightly with increasing coolant argon flow rate. After 14 liters/min, the emission intensities begin to level off. The background is constant but the peak-to-peak noise decreases exponentially with increasing flow rate. An optimum in the signal/noise ratio is observed at approximately 12 liters/min.

Within the flow rate range studied, atomic emission intensities and background and noise intensities did not vary with the plasma argon flow rate. The plasma argon was employed merely to prevent damage to the torch during sample introduction. Without any plasma gas flow rate, the discharge was observed to come into contact with the plasma and sample tubes during the introduction or organic species.

Several workers including Kirkbright, et al, have reported that atomic emission intensities pass through a maximum as the sample gas flow rate is increased; however, their effect is not observed in the present study. The carbon emission intensity is found to increase linearly with decreasing flow rate for flow rates from 0.7 to 2.0 liters/min. Each liter per minute increase in flow rate results in a 55% reduction in observed emission intensity. Background and noise, at the atomic carbon wavelength, do not change appreciably within this range of sample gas flow rates. The diameter of the relatively low temperature "hole" in the plasma, through which the sample is introduced, is observed to decrease with the flow rate and is found to result in a decrease in the stability of the plasma during sample introduction. A compromise between intensity and stability is observed at a flow rate of approximately 0.9 liter/min. The effects of the coolant, plasma, and sample argon flow rates on atomic emission intensities are found to be the same for all of the elements studies.

Another matter of interest involves the well known fact that atomic emission intensities vary with height in the ICP. In the present, a single height was located at which all the elements of interest could be determined without any significant loss of sensitivity for any particular element. Thus, as can be noted in Table III, although the vertical position of maximum response is not the same for all the elements, employment of a compromise height of 9 mm above the top of the load coil results in a loss in sensitivity of only 5% for hydrogen and 3% or less for all the other elements. Further studies to be described were performed at this compromised position.

TABLE III

| Emission intensities as a function of the height in the plasma | | | |
|---|---|---|---|
| Element | Wavelength (Å) | Position Maximum (mm) | Signal Loss at 9 mm (%) |
| B | 2497.7 | 6 | 3 |
| C | 2478.6 | 9 | 0 |
| H | 4861.3 | 6 | 5 |
| I | 2061.6 | 3 | 1 |
| P | 2136.2 | 12 | 3 |
| S | 1900.3 | 12 | 0 |
| Si | 2516.1 | 9 | 0 |

With regard to emission spectra, the atomic and molecular emissions observed in the ICP are summarized in Tables IV and V, respectively, along with their observed relative intensities at the height of 9 mm in the plasma.

TABLE IV

| Wavelengths and relative intensities of observed atomic lines at a height of 9 mm in the ICP. | | |
|---|---|---|
| Element | Wavelength (Å) | Relative intensity |
| B | 2088.8 | 140 |
| | 2089.3 | 120 |
| | 2496.8 | 120 |
| | 2497.7 | 610 |
| C | 1930.9 | 80 |
| | 2478.6 | 100 |
| H | 4861.3 | 30 |
| | 6562.9 | 10 |
| I | 2061.6 | 40 |
| P | 2136.2 | 270 |
| | 2149.1 | 160 |
| | 2152.9 | 20 |
| | 2534.0 | 40 |
| | 2535.6 | 150 |
| | 2553.3 | 30 |
| | 2554.9 | 30 |
| S | 1900.2 | 1.3 |
| | 1914.7 | 0.6 |
| | 2168.9 | 1.0 |
| | 2190.6 | 0.1 |
| Si | 2208.0 | 190 |
| | 2210.9 | 360 |
| | 2214.7 | 130 |
| | 2216.7 | 680 |
| | 2218.1 | 260 |
| | 2506.9 | 1070 |
| | 2514.3 | 1480 |

TABLE IV-continued

Wavelengths and relative intensities of observed atomic lines at a height of 9 mm in the ICP.

| Element | Wavelength (A) | Relative intensity |
|---|---|---|
| | 2516.1 | 3230 |
| | 2518.3 | 740 |
| | 2519.2 | 680 |
| | 2524.1 | 870 |
| | 2528.5 | 1070 |
| | 2880.6 | 2360 |

TABLE V

Wavelengths and relative intensities of the observed molecular band heads at a height of 9 mm in the plasma.

| Species | Wavelength (Å) | Relative intensity |
|---|---|---|
| $C_2$ | 4365.2 | 4 |
| | 4371.4 | 2 |
| | 4382.5 | 1 |
| | 4678.6 | 8 |
| | 4684.8 | 8 |
| | 4697.6 | 10 |
| | 4715.2 | 10 |
| | 4737.1 | 10 |
| | 5129.3 | 15 |
| | 5165.2 | 40 |
| CH | 4312.5 | Weak[a] |
| | 4315.0 | Weak |
| CN | 3583.8 | 40 |
| | 3585.9 | 40 |
| | 3590.4 | 30 |
| | 3850.9 | 8 |
| | 3854.7 | 8 |
| | 3861.9 | 50 |
| | 3871.4 | 40 |
| | 3883.4 | 80 |
| | 4153.4 | 8 |
| | 4167.8 | 8 |
| | 4181.0 | 20 |
| | 4197.0 | 30 |
| | 4216.0 | 30 |
| CS | 2575 | 60 |
| | 2593 | 70 |
| | 2606 | 50 |
| | 2622 | 30 |
| | 2663 | 20 |
| NH | 3360 | Weak |
| | 3370 | Weak |
| OH | 3067.2 | Weak |
| | 3089 | Weak |

[a]Weak represents a relative intensity of less than 1.

The emission intensities reported are measured relative to the 2478.6 Å atomic carbon emission intensity produced by 1 µg of carbon from n-heptane. This emission intensity, which corresponds to $7.8 \times 10^{-2}$ µA of photomultiplier current at a photomultiplier tube voltage of 500 V, is defined as 100. The atomic and molecular emission intensities are not corrected for the transfer functions of the optics and the detector.

Two strong lines originating from atomic carbon occur at 1930.9 and 2478.6 Å. The Hα and Hβ lines at 6562.8 and 4861.3 Å, respectively, are present but at lower intensities than the carbon lines. Molecular band spectra (Table V) can be observed. The $N_2$ and $O_2$ required to form CN, NH, and OH molecules, when hydrocarbons are added to the plasma, most likely result from impurities in the argon supplies. Additionally, CS band emission has been observed for sulfur-containing compounds. The variation in emission intensities with vertical position for the carbon-containing species $C_2$, CH, CN, and CS are qualitatively the same as for the atomic emission intensities studied. These diatomic species exhibit intensity maxima at approximately 9 mm above the load coil. At this position, the $C_2$, CN and CS band spectra are moderately strong but the CH band spectrum is very weak. The NH and OH band spectra, produced when nitrogen- and oxygen-containing compounds are introduced into the plasma, are very weak at a height of 9 mm in the plasma. However, the intensity of these band spectra increased higher up in the plasma and intensity maxima are observed at a height which corresponds approximately to the end of the coolant tube. This effect has been previously observed. However, $C_3$ emission and the CCl and PO band spectra previously found in the MEP were not observed. Organic compounds containing sulfur, phosphorus, iodine, boron and silicon exhibit atomic spectra originating from these elements.

Another pertinent consideration affecting the present detection procedures involves the selection for optical monitoring purposes of optimum atomic lines, i.e. line selection. Thus, for those elements whose most intense atomic line falls between 1900 and 3000 Å, no spectral interferences are observed due to argon lines or molecular band heads as there are no recorded Ar (I) or Ar (II) lines between 1066.7 and 3000.4 Å, and no observed lines for higher ionization states between 1900 and 3000 Å. The only observed molecular band emissions in this spectral region arise from the CS molecule and the resulting band heads are not close to any of the major atomic lines used for analysis in these studies. Therefore, with the exception of hydrogen, detection limits are determined at the most intense atomic lines. In the present experimental configuration, the 4861.3 Å hydrogen line is 4 times more intense than the 6562.8 Å line. However, the 4861.3 Å line is partially overlapped by scattering from the intense 4876.3 Å argon line. When an organic sample is introduced into the plasma, the intensity of the argon line decreases resulting in a decrease in the background at 4861.3 Å. The net change in the signal intensity at 4861.3 Å (emission intensity and background intensity) is zero when the weight of hydrogen introduced is approximately 200 ng. This problem is not encountered at the 6562.8 Å line. Thus, the detection limit for hydrogen is found to be better at the less intense 6562.8 Å line than at the 4861.3 Å line, although the use of automatic background correction might make it possible to use the more intense 4861.3 Å line for analysis. Use of a 5000 Å blaze grating and a more red-sensitive photomultiplier tube will, no doubt, improve the detection limit at the 6562.8 Å line.

Detection limits determined at atomic wavelengths are presented in Table VI. Detection limits are defined as the weight of a given element which produces a signal equal to twice the peak-to-peak noise. For carbon and iodine these detection limits are comparable to the state of the art values reported for the MEP but the detection limit for sulfur was found to be not as good in the ICP as it is in the MEP. With the exception of phosphorus, upper limits of the dynamic ranges are not limited by the linearity of the working curves but by the weight of a given compound which can be introduced without overloading the plasma. The phosphorus working curve is the only one which is observed to deviate from linearity at higher concentrations.

No boron, iodine, phosphorus, sulfur, or silicon impurities are observed in the argon. The argon was found to contain approximately 7 ppm of carbon. Also, no background hydrogen was observed with the present optical configuration. Detection limits are determined by measuring the increase in emission intensity, at an atomic wavelength, when a compound containing a given element is introduced into the plasma. For this reason, the carbon present in the argon contributes a small but constant signal to the background at the carbon wavelength.

TABLE VI

Detection limits and dynamic ranges.

| Element | Wavelength (Å) | Detection limit (ng) | Dynamic range |
|---|---|---|---|
| B | 2497.7 | 1 | $1 \times 10^3$ |
| C | 2478.6 | 12 | $2 \times 10^3$ |
| H | 6562.8 | 27 | $1 \times 10^2$ |
| I | 2061.6 | 4 | $1 \times 10^5$ |
| P | 2136.2 | 0.6 | $2 \times 10^4$ |
| S | 1900.3 | 250 | $1 \times 10^2$ |
| Si | 2516.1 | 0.8 | $5 \times 10^2$ |

To make most efficient use of ICP-OES for the elemental analysis of organic compounds, the emission intensities per unit weight of the elements (response factors) should be the same for all compounds containing these elements. This condition will not be met if the relative thermal degradation efficiency varies between compounds or if an appreciable and variable fraction of the atoms produced by thermal degradation recombine to form diatomic molecules before they pass above the observation zone of the plasma. Fewer diatomic species have been observed in the ICP than in the MEP. It has also been noted that the formation of carbon and sulfur deposits on the quartz excitation cell of the MEP can affect the response factors for these elements. The premise, that the emission intensity per unit weight is independent of structure in the ICP, is evaluated by determining carbon response factors for a variety of organic compounds containing a variety of functional groups. These results, presented in Table VII, show that for most compounds the length of the carbon chain and the types of functional groups attached to it do not significantly affect the carbon response. The only exceptions noted are the low response factor of pyridine and the abnormally high response factors for compounds containing large chlorine/ or bromine/carbon ratios such as ethyl bromide and trichloroethylene. The low response for pyridine is probably due to incomplete thermal degradation of the stable aromatic nitrogen ring. No explanation for the enhancement of the carbon emission by bromine and chlorine has as yet been found. No carbon, sulfur, or phosphorus deposits were visible on the inside of the coolant tube even after extended periods of use.

TABLE VII

Relative response factors of organic compounds at the 2478.6 Å atomic carbon line.

| Empirical formula | Compound | Response factor[a] |
|---|---|---|
| $CS_2$ | Carbon disulfide | 99 |
| $C_2H_3Cl_3$ | Trichloroethylene | 123 |
| $C_2H_3N$ | Acetonitrile | 104 |
| $C_2H_5Br$ | Ethyl bromide | 118 |
| $C_2H_5I$ | Ethyl iodide | 101 |
| $C_2H_6O$ | Ethyl alcohol | 99 |
| $C_3H_7N$ | η-Propylamine | 103 |
| $C_4H_4S$ | Thiophene | 99 |
| $C_4H_8O_2$ | Ethyl acetate | 105 |
| $C_4H_9Br$ | 2-Bromo-2-methylpropane | 104 |
| $C_4H_9Cl$ | 1-Chloro-2-methylpropane | 105 |
| $C_4H_9Cl$ | 1-chlorobutane | 104 |
| $C_4H_9I$ | 2-Iodobutane | 103 |
| $C_5H_5N$ | Pyridine | 86 |
| $C_5H_8O_2$ | 2,4-Pentanedione | 96 |
| $C_5H_{10}Br_2$ | 1,5-Dibromopentane | 95 |
| $C_5H_{11}Br$ | 1-Bromo-3-methylbutane | 101 |
| $C_6H_6$ | Benzene | 100 |
| $C_6H_{12}$ | 1-Hexene | 102 |
| $C_6H_{12}$ | Cyclohexane | 97 |
| $C_7H_8$ | Toluene | (100) |
| $C_7H_{16}$ | η-Heptane | 100 |
| $C_9H_{12}$ | Cumene | 98 |

[a]The response for 1μg of carbon from toluene is defined as 100.

The results of this study demonstrate that the use of ICP-OES for the elemental analysis of a number of non-metallic species in organic compounds is a viable technique. The method is sensitive with observed detection limits in the low nanogram region and working curves are found to be linear over 2 to 5 orders of magnitude. With the proper choice of atomic lines for analysis, no significant spectral interferences are observed. A comparison of the atomic and molecular emission intensities in the ICP with those observed in the MEP suggests that the ratio of atomic to molecular emissions is greater in the ICP. The fact that the carbon emission intensity per unit weight is approximately the same for a wide variety of compounds demonstrates that molecular degradation is essentially complete and that only a small fraction of the atoms produced recombine to form diatomic species. Due to the fact that the sample does not come into contact with the outer quartz tube, no carbon, sulfur, or phosphorus deposits have been observed even after extended periods of use. The current optical system limits the technique to the determination of elements with atomic emission lines between 1900 and about 6500 Å. This provides the capability for analysis of boron. carbon, hydrogen, iodine, phosphorus, silicon, and possibly sulfur. Extension of the wavelength range to include near ir lines and vacuum ultraviolet lines promises to extend the range of the method to include the analysis of bromine, chlorine, fluorine, nitrogen, and oxygen at atomic lines.

Further experimental work demonstrates the applicability of the ICP to the simultaneous multi-element analysis of the gaseous effulents from a gas chromatograph as well as other applications requiring simultaneous multi-element analysis of molecular compounds. In this work a gas chromatograph 16 (FIG. 1) can be used to elute the sample through a 'make up' splitter 16a to inductively coupled plasma torch 7. A direct reader 18 monitors the sample emissions to provide parallel outputs to electrometers 19 supplying amplified signals through a multiplexer and A-D converter 21 to a computer 22. The plasma torch, however, is modified to the extent that coolant tube 9 (FIG. 2) is extended 10.5 cm above the top of the load coil and sample tube 12 replaced with a 7 mm o.d. 1 mm i.d. capillary tubing. All observations were made 9 mm above the load coil viewing the plasma discharge through the coolant tube. A more detailed description of these components will be provided subsequently.

As indicated, the study demonstrates the ability of the ICP to perform simultaneous multi-element analysis on each component of a mixture. ICP detection limits, linear dynamic ranges and selectivity compare favorably with those observed for flame photometric detectors (FPD) and microwave-excited plasma detectors (MEPD). Flame detectors, for example, yield high sensitivity for some elements but they suffer disadvantages with respect to simultaneous multi-element analysis. Thus, to achieve their reported sensitivity, conditions often must be optimized for each element. Additionally, the relatively low temperatures of most chemical flames seriously limits the analysis of many non-metalic elements by atomic emissions spectrometry (AES).

Difficulties in performing simultaneous multi-element analysis also are reported with the MEPD. In some cases, atomic emission intensities vary with molecular structure. Recombination reactions appear to be extensive. As with flames, molecular band heads can limit general applicability. Further, as a practical matter, the MEPD also may suffer from the formation of deposits on the inside of the excitation cells. Although molecular oxygen and nitrogen have been employed as scavenger gases, internal etching and depositions still occur indicating the desirability of completely eliminating the need to view through a cell wall.

In the ICP application, oxygen or nitrogen does not need to be added to the plasma to reduce deposits. While deposits sometimes may form, they are not a problem since they are well above the observation zone. Also, unlike flames, all analyses can be performed with a single set of operating conditions. Since only atomic lines are employed, problems associated with diatomic band heads are avoided.

ICP detection limits, linear dynamic ranges and selectivities generally compare quite favorably with those for the FPD and MEPD. For metallic elements and non-metallic elements with relatively intense atomic lines, detection limits are in the low nanogram range and both linear dynamic ranges and selectivities are $10^3$ or greater. Table VIII provides the ICP detection limits and linear dynamic ranges.

TABLE IX

Comparison of ICP selectivities with those for the FPD & MEPD.

| Element | Selectivity Ratio | | |
|---|---|---|---|
| | ICP | FDP | MEPD |
| Cl | 60 | — | 30 |
| H | $3 \times 10^3$ | — | — |
| I | $1 \times 10^3$ | — | — |
| Si | $3 \times 10^4$ | — | 20 |
| Fe | $1 \times 10^3$ | $1 \times 10^4$ | — |
| Pb | $3 \times 10^3$ | $1 \times 10^3$ | — |
| Sn | $3 \times 10^4$ | $2 \times 10^3$ | — |

Empirical Formula Determinations With An ICP-GC Detector

The described simultaneous multi-element capabilities of inductively-coupled plasma emission spectrometry can be used to determine the empirical formula of compounds eluted from the gas chromatograph. As will be recognized, empirical formula determinations generally depend upon measurements of the relative ratios of elemental constituents. Through the use of high speed computer controlled data acquisition, data describing the relative atomic ratios of the elements composing the eluting compound can be acquired as the elution concentration increased to a maximum peak height and subsequently falls. This, in turn, yields a large number of elemental ratio determinations covering a wide range of analyte concentrations at the detector. The computer subsequently selects those ratio determinations falling within the observed linear response range and averages them to obtain the best accuracy.

ICP determination of empirical formulas apparently is achieved because the relative response of a given species is less sensitive to molecular structure than in

TABLE VIII

Comparison of Observed ICP detection limits and Linear Dynamic Ranges with Flame Emission and Microwave Emission Plasma GC Detectors

| | | Detection Limit (ng) | | | | Linear Dynamic Range | | |
|---|---|---|---|---|---|---|---|---|
| | Atomic | | FPD | | | | | |
| Element | Wavelength (Å) | ICP | Air-Rich | H-Rich[a] | Argon MEPD[d] | ICP | FPD | MEPD[d] |
| Br | 7005.7 | $2 \times 10^5$ | — | — | — | Poor | — | $1 \times 10^3$ |
| C | 2478.6 | 12 | $4 \times 10^{3a}$ | $1 \times 10^4$ | — | $1 \times 10^3$ | $1 \times 10^{2a}$ | $1 \times 10^3$ |
| Cl | 7256.7 | $7 \times 10^3$ | — | — | 12 | $1 \times 10^2$ | — | $1 \times 10^2$ |
| F | 6348.5 | $1 \times 10^6$ | — | — | 70 | Poor | — | — |
| H | 6562.8 | 5.5 | — | — | — | $1 \times 10^3$ | — | — |
| I | 2061.6 | 24 | $10^b$ | — | 22.4 | $1 \times 10^3$ | $1.4 \times 10^{2b}$ | $1 \times 10^2$ |
| Si | 2516.1 | 0.8 | $0.4^c$ | — | — | $5.10^3$ | $10^c$ | — |
| Fe | 3719.9 | 5.9 | $2^c$ | 0.8 | — | $2.10^4$ | $1 \times 10^{2a}$ | — |
| Pb | 2170.0 | 33 | $40^b$ | 5 | — | $1 \times 10^3$ | $1 \times 10^{3a}$ | — |
| Sn | 2840.0 | 0.9 | $5^b$ | 5 | — | $1 \times 10^4$ | $1 \times 10^{2a}$ | — |

[a]Aue and Hill (1973)
[b]Sevcik (1976, p. 161)
[c]Gutsche and Herrmann (1971)
[d]Dagnall et al (1972b)

Another important capability of any element selective detector is its ability to provide independent determinations for each element. The simultaneous multi-element capability of the ICP is especially suited to this application. To evaluate the selectivity of the ICP GC detector, selectivity ratios versus atomic carbon at 2478.6 Å were determined and are provided in Table IX. The particular ratios are known to be limited by certain uncompensated background changes and they can be improved considerably by employing automatic background correction techniques.

the argon supported MEP. In this regard, sensitivity variations could seriously limit the ability to accurately determine the empirical formulas if, for example, a partial degradation should result in a preferential production of atomic species of certain elements. On the other hand, if a percentage of the compound is not completely degraded and passes through the plasma without producing atomic degradation products, the relative ratios will not be affected and the empirical formula results will be correct.

Molecular formula determinations also can be made by utilizing the emipirical formula data. Under constant chromatographic conditions the number of carbon atoms for a given class of molecules is proportional to a constant times the log of the components retention time or, the time (corrected for dead volume) between injection of a mixture and the elution of a given component. A proper constant for a given class of molecule can be selected based on knowledge of the component's empirical formula.

Empirical formula determination, as will be understood, is based upon an ability to generate data indentifying the specific fractions of each element present in the compound. If, for example, the specific fractions of elements present in an unknown compound are $P_c$, $P_h$ and $P_x$ (c, h and x denoting carbon, hydrogen and element x respectively) values for those fractions must be obtained. In the present systems, the specific fraction values are obtained from the detected emission or response data. In particular, $P_c$, $P_h$ and $P_x$ each can be mathematically defined in terms of the relationship responses between, i.e. ratios of, certain known constant values. The following rationale provides these relationships:

If it is initially assumed that when an organic compound of molecular formula $C_p$, $H_q$ and $X_r$ enters the plasma it is thermally decomposed completely to atomic species, the thermal reaction can be given as:

$$C_pH_qX_r \xrightarrow{\Delta} pC + qH + rX \quad (1)$$

If the response versus weight curve for each element, produced by Reaction 1, is linear, then an analytical calibration curve of the form:

$$R_i^o = m_i w_i^o + b_i \quad (2)$$

will describe the emission response of each element. For the $i^{th}$ element: $R^o$ is the response, m the slope of the line, $w^o$ the weight of the element, and $b_i$ the intercept of the response axis. If $b_i$ can be either made to equal zero or much less than $m_i w_i^o$, equation 2 can be reduced to:

$$R_i^o = m_i w_i^o \quad (3)$$

The total weight of a given element ($W_i^o$) is the sum of the weight produced by an added compound ($w_i$) and the weight contributed by impurities in the argon ($w_i'$). Thus, equation 3 becomes:

$$R_i^o = m_i w_i + m_i w_i' \quad (4)$$

The term $m_i w_i'$ in equation 4 represents the background and emission from impurity elements ($R_i'$). If this term is actually due to a constant impurity in the argon, it can be subtracted out and the net emission intensity is then given by:

$$R_i = m_i w_i \quad (5)$$

The weight of each element, from an added compound, is given by:

$$w_i = P_i W \quad (6)$$

where $P_i$ is the fraction of element i in the compound and W is the total weight of the compound. Under this condition, equation 5 becomes:

$$R_i = m_i P_i W \quad (7)$$

Assuming the response per unit weight for each element to be independent of the compound containing the elements, the ratios of the slopes of the working curves will be constants:

$$K_1 = \frac{m_c}{m_h} = \frac{R_c P_h}{R_h P_c}; \quad (8\text{-}10)$$

$$K_2 = \frac{m_c}{m_x} = \frac{R_c P_x}{R_x P_c}; \quad K_3 = \frac{m_h}{m_x} = \frac{R_h P_x}{R_x P_h}$$

where the subscripts c, h and x denote carbon, hydrogen and element X respectively. Equations 8-10 contain only two independent equations since, for example, $K_3 = K_2/K_1$. Equation 11 constitutes the third independent equation required to define the system:

$$P_c + P_h + P_x = 1 \quad (11)$$

If one compound is used to determine the constants $K_1$ and $K_2$, then the values of $P_c$, $P_h$ and $P_x$ for an unknown compound can be determined from the emission responses ($R_c$, $R_h$ and $R_x$) for the compound:

$$P_c = \frac{R_c}{R_c + K_1 R_h + K_2 R_x} \quad (12)$$

$$P_h = \frac{K_2 R_h P_c}{R_c} \quad (13)$$

$$P_x = \frac{K_2 R_x P_c}{R_c} \quad (14)$$

For the special case of hydrocarbons, $R_x = P_x = 0$. However, problems would occur if recombination to form diatomics occurred to an appreciable extent, i.e.:

$$H + O \rightarrow OH$$

$$C + O \rightarrow CO \text{ etc.}$$

Previous studies, however, have shown that recombination is not a major source of interference.

As has been noted, the foregoing is based upon an initial assumption that organic compounds entering the plasma are thermally decomposed completely to atomic species. If thermal degradation is not complete, equations 8-10 may or may not be valid depending upon the resulting decomposition products. Furthermore, the assumption that the response per unit weight for each element is independent of structure also may not be a valid assumption.

Incomplete thermal decomposition may result from some molecules passing through or around the plasma discharge without any decomposition;

$$C_pH_qX_r \xrightarrow{\Delta} f[pC + qH + rX] + [1 - f]C_pH_qX_r \quad (15)$$

where f is the fraction of molecules decomposed. In this case, W can be replaced fy fW in Equations 6 and 7. Equations 8-10 and 12-14 are not altered by this substitution. The possibility of partial thermal decomposition of individual molecules producing non-stoichiometric atomic concentrations is a more serious consideration.

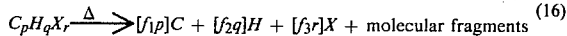

$$C_pH_qX_r \xrightarrow{\Delta} [f_1p]C + [f_2q]H + [f_3r]X + \text{molecular fragments} \quad (16)$$

where $f_1$, $f_2$ and $f_3$ are the fractions of carbon, hydrogen and element X, respectively, are produced by partial thermal decomposition. In this case, equation 7 becomes:

$$R_1 = m_1P_1f_1W \quad (17)$$

and the fractions $f_1$ are retained in equations 6–8. If this should occur to any significant degree, equations 12–14 would no longer be valid.

The validity of the present study and, in particular, the validity of its assumptions, rests upon the actual performance of the ICP in determining empirical formulas. If, as will be shown, experimental values obtained from the ICP agree with theoretical values, equations 12–14 are valid and the possibility that partial thermal decomposition produces non-stoichiometric atomic concentrations is not a matter of serious concern.

Before describing experimental results, the actual experimental configuration and its operation should be considered. As will be noted, it is similar in many respects to that used on establishing the simultaneous multi-element detection capability. Thus, it uses torch 1, RF supply 2, matching network 3, multichannel spectrometer 18, and a gas chromatograph sampling system including chromatograph 16 and splitter 16a. However, instead of relying upon the recording of the response data, the empirical formula system employs controlled data acquisition components such as FET electrometers 19, a multiplexer and A-D converter 21 and a computer 22 all of which will be further identified. All experiments used a single set of plasma operating conditions. Forward power of 800 watts at 27.12 MHz was employed. A region 9 mm above the load coil was used. Coolant, plasma and sample argon were operated at 12, 0.5 and 0.9 L/min., respectively. The torch, as in previous experiments, is a capillary tube (0.1 mm) to decrease dead volume and obtain narrow peaks. Scanning monochrometer 4 can be used to supplement the emission information.

To obtain the desired parallel outputs from the excited atomic species, spectrometer 18 can be a Jarrell-Ash (Waltham, MA) Model 66-100 1.5 meter Paschen-Runge direct reader having a 200 micrometer entrance and 75 micrometer exit slits. The low level currents from each exit slit are applied to the series of FET electrometers 19 and a National Semiconductor (Santa Clara, CA) Model LF-13508 analog multiplexer is interfaced through a Burr-Brown (Tucson, AZ) ADC 80-AG-10 analogue to digital converter to a Hewlett-Packard (Palo Alto, CA) 2116 C minicomputer equipped with 16 K of memory. The electrometers convert the low level output currents to high level voltages. They are operated with a time constant of less than 100 microseconds. Also, in the experimental arrangement, the FET electrometers are sampled sequentially but at a rate of 1.6 KHz to provide essentially a simultaneous readout of the parallel outputs. Other arrangements using conventional sample and hold techniques can be used to make the readout actually simultaneous. Thus, the parallel emission responses can be considered as being essentially instantaneous or, in other words, as providing discrete response ratios at any given instant in the sampling period. To provide the discrete values, the high speed scans are performed successively with a particular delay time between each scan so that, over the entire scanning period, a large number of ratios are provided. If desired, the delay time between the high speed scans can be software-selectable based upon a crystal controlled real-time-clock.

Typical response peaks yielded 200 such elemental ratios determinations subsequently were averaged in computer 22 to produce the values shown in Tables X–XIV. The large number of ratios is obtained by extending the successive high speed scans over the period required for the elution of the compound into the plasma torch. As will be appreciated, the concentration of the eluted gas varies constantly during this period in that the concentration rises to a peak and then falls off to zero. In averaging the ratios, non-linear portions can be discarded.

The sampling system itself is a Varian (Walnut Creek, CA) Model 1520 gas chromatograph equipped with a Model D2-1866 automatic linear temperature programmer. The column employed is a six-foot, 3.175 mm o.d. column packed with 8% carbon wax 1540 on 80/100 fire brick. The output of the column is connected directly to a 1/57 mm swagelok "T". One branch of the T is the "make-up" argon (0.9 L/min.) and the third branch, as shown, goes to the sample tube of the plasma torch. All three agents were "A.R. grade" used without further purification.

RESULTS

To evaluate the accuracy and precision of the method and determine which of the simplifying assumptions are warranted, the hydrogencarbon and carbon/hydrogen/halogen percentage composition for a series of hydrocarbons and halogenated were determined. The data given in Tables X and XI demonstrate close agreement between theoretical and experimental values. Reproducibility data are given in Tables XII and XIII.

TABLE X

Elemental analysis of hydrocarbons

|  | % Carbon | | Relative Difference (%) | % Hydrogen | | Relative Difference (%) |
|---|---|---|---|---|---|---|
|  | Theoretical | Found |  | Theoretical | Found |  |
| cumene | 90.00 | 89.72 | 0.31 | 10.00 | 10.28 | 2.80 |
| cyclohexene | 87.80 | 87.94 | 0.16 | 12.20 | 12.06 | 1.15 |
| ethylbenzene | 90.57 | 90.57 | 0.00 | 9.43 | 9.43 | 0.00 |
| n-heptane | 84.00 | 83.92 | 0.10 | 16.00 | 16.08 | 0.50 |
| isooctane | 84.21 | 84.15 | 0.07 | 15.79 | 15.85 | 0.38 |
| methylcyclohexane | 85.71 | 85.72 | 0.01 | 14.29 | 14.28 | 0.07 |
| 1-pentene | 85.71 | 85.98 | 0.32 | 14.29 | 14.02 | 1.89 |
| o-xylene | 90.67 | 90.67 | 0.00 | 9.43 | 9.43 | 0.00 |
| m-xylene | 90.57 | 90.48 | 0.10 | 9.43 | 9.52 | 0.95 |

TABLE XI

Elemental analysis of halogens.

|  | % Carbon | | Difference | | Average Standard Deviation |
|---|---|---|---|---|---|
|  | Theoretical | Found | Absolute | Relative | (parts/thousand) |
| 1-iodobutane | 26.10 | 25.86 | 0.24 | 0.92 | 12.3 |
| 2-iodobutane | 26.10 | 26.40 | 0.30 | 1.15 | 10.9 |
| iodobenzene | 35.32 | 35.07 | 0.25 | 0.71 | — |
| 1-chlorobutane | 51.90 | 51.81 | 0.09 | 0.17 | 2.8 |
|  | % Hydrogen | | | | |
|  | Theoretical | Found | | | |
| 1-iodobutane | 4.89 | 4.84 | 0.05 | 1.02 | 7.3 |
| 2-iodobutane | 4.89 | 4.88 | 0.01 | 0.20 | 9.9 |
| iodobenzene | 2.47 | 2.31 | 0.16 | 6.5 | — |
| 1-chlorobutane | 9.80 | 9.73 | 0.07 | 0.71 | 8.6 |
|  | % Halogen | | | | |
|  | Theoretical | Found | | | |
| 1-iodobutane | 69.00 | 69.31 | 0.31 | 0.45 | 1.4 |
| 2-iodobutane | 69.00 | 68.72 | 0.28 | 0.41 | 1.4 |
| iodobenzene | 62.21 | 62.61 | 0.40 | 0.64 | — |
| 1-chlorobutane | 38.30 | 38.46 | 0.16 | 0.42 | 4.9 |

TABLE XII

Repetive analysis of hydrocarbons.

|  | Cyclohexene | | m-Xylene | |
|---|---|---|---|---|
|  | % C | % H | % C | % H |
| Run 1 | 88.07 | 11.93 | 90.54 | 9.46 |
| Run 2 | 87.98 | 12.02 | 90.63 | 9.37 |
| Run 3 | 88.06 | 11.94 | 90.43 | 9.57 |
| Run 4 | 87.76 | 12.24 | 90.37 | 9.63 |
| Run 5 | 87.85 | 12.15 | 90.38 | 9.62 |
| Average | 87.94 | 12.06 | 90.47 | 9.52 |
| $\bar{\sigma}$ (ppt) | 1.5 | 11.2 | 1.2 | 11.8 |

TABLE XIII

Precision and accuracy for the elemental analysis of organic compounds.

| % of Element in Compound | Average Difference % | | Average Standard Deviation (parts/thousand) |
|---|---|---|---|
|  | Absolute | Relative |  |
| 50 | 0.14 | 0.19 | 1.7 |
| 10–50 | 0.17 | 1.03 | 9.8 |
| 1–10 | 0.08 | 1.21 | 9.4 |

Empirical formulas are determined from elemental compositions. For hydrocarbons, the experimental H/C ratios are compared to those for hydrocarbons containing 20 or less carbon atoms. Table XIV lists the empirical formula for each compound whose H/C ratio is closest to the experimental value.

TABLE XIV

Empirical formulas for a variety of hydrocarbons studied whose hydrogen to carbon atomic ratio is closest to the experimentally determined hydrogen to carbon ratios.

|  | Empirical Formula | H/C Atomic Ratio | | % Difference | |
|---|---|---|---|---|---|
|  |  | Theoretical | Found | Absolute | Relative |
| cumene | C₃H₄ | 1.333 | 1.376 | 00.43 | 3.23 |
| cyclohexene | C₃H₅ | 1.667 | 1.646 | 0.021 | 1.26 |
| ethylbenzene | C₄H₅ | 1.250 | 1.249 | 0.001 | 0.08 |
| n-heptane | C₇H₁₆ | 2.286 | 2.299 | 0.013 | 0.57 |
| isooctane | C₄H₉ | 2.250 | 2.260 | 0.010 | 0.44 |
| methylcyclohexane | CH₂ | 2.000 | 1.999 | 0.001 | 0.05 |
| 1-pentene | CH₂ | 2.000 | 1.957 | 0.043 | 2.15 |
| o-xylene | C₄H₅ | 1.250 | 1.249 | 0.001 | 0.08 |
| m-xylene | C₄H₅ | 1.250 | 1.263 | 0.013 | 1.04 |

To determine the empirical formulas for halogen compounds, the percentage composition for each element found in the compound first is divided by the atomic weight of that element. These ratios then are adjusted so that the halogen ratio is 'one' as shown in table XV. Empirical formulas then are obtained by rounding off the carbon and hydrogen ratios to the nearest whole number. In all cases, the correct empirical formula is obtained.

TABLE XV

Experimentally determined Empirical formulas for halogenated compounds.

|  | Normalized Atomic Ratios | | | Empirical Formula |
|---|---|---|---|---|
|  | C | H | X |  |
| 1-iodobutane | 3.94 | 8.86 | 1.00 | C₄H₉I |
| 2-iodobutane | 4.06 | 9.00 | 1.00 | C₄H₉I |
| iodobenzene | 5.92 | 4.69 | 1.00 | C₆H₅I |
| 1-chlorobutane | 3.98 | 8.97 | 1.00 | C₄H₉Cl |

Molecular formulas for hydrocarbons are deduced from experimental empirical formulas by utilizing the so-called retention time data. This data can be obtained directly from the torch since its emission responses are present only during the elution period of the compound from the chromatograph. Retention times ($T_r$) are used to determine approximate carbon numbers (n) according to the following relationship:

$$n \propto k \log T_r$$

where k is an experimental constant. Constant k depends upon chromatographic conditions and the class of the compound. For present purposes, two classes of compounds (aromatic and non-aromatic) are considered. To characterize the retention properties of the GC column, the ratio of the carbon number to the log of the retention time for a series of aromatic and non-aromatic compounds is determined. For each class of compounds, the average of these ratios is taken as the constant k in $n = k \log T_r$. Observed constants of 11.7 and 22.7 are found for aromatic and non-aromatic respectively. The decision as to which constant to employ is based upon the experimental H/C ratios. Compounds with ratios of 1.5 or less are classed as aromatic and compounds with ratios greater than 1.5 as non-aromatic. The molecular formulas determined by this method are listed in table XVI.

TABLE XVI

Molecular formulas determined from the experimental empirical formula data and retention times.

| Compound | Retention Time (min) | nC | Empirical Formula | Molecular Formula |
|---|---|---|---|---|
| cumene | 6.40 | 9.4 | $C_3H_4$ | $C_9H_{12}$ |
| cyclohexene | 2.10 | 7.3 | $C_3H_5$ | $C_6H_{10}$ |
| ethylbenzene | 5.45 | 8.6 | $C_4H_5$ | $C_8H_{10}$ |
| n-heptane | 1.95 | 6.6 | $C_7H_{16}$ | $C_7H_{16}$ |
| isooctane | 1.98 | 6.7 | $C_4H_9$ | $C_8H_{18}$ |
| methylcyclohexane | 2.00 | 6.8 | $CH_2$ | $C_7H_{14}$ |
| 1-pentane | 1.75 | 5.5 | $CH_2$ | $C_6H_{12}$ |
| o-xylene | 6.85 | 9.8 | $C_4H_5$ | $C_8H_{10}$ |
| m-xylene | 5.55 | 8.7 | $C_4H_5$ | $C_8H_{10}$ |

Summarizing the foregoing, it first has been demonstrated that an inductively-coupled plasma can provide highly accurate relative elemental composition analysis when coupled to a gas chromatograph. Further, the observed accuracy and precision for the compounds studied are at a sufficiently high level to allow calculation of reliable empirical formulas. The observed empirical formula subsequently can be used to choose a constant and estimate an approximate carbon number. Only approximate numbers are needed since the molecular formula must be a whole number multiple of the empirical formula.

As has been noted in an earlier part of this discussion, usable lines for atomic oxygen and atomic nitrogen have not as yet been observed. Until suitable lines are found, care should be exercised. While relative ratios of measured atomic constituents will remain accurate, the calculated empirical formulas will not reflect elements not observed. Further, use of retention times for calculating a carbon number under such conditions also may lead to error. However, even considering these limitations, the high degree of quantitative accuracy and the large number of elements which can be determined should make ICP-GC empirical formula determinations a highly valuable procedure for use by both analytical and organic chemists.

Obviously many modifications and variations of the present invention are possible in the light of the above teachings. It is therefore to be understood that within the scope of the appended claims the invention may be practiced otherwise than as specifically described.

We claim:

1. A method employing a gas chromatograph and an inductively-coupled plasma torch for evaluating the atomic elements of molecular compounds comprising;
   processing said compound through said chromatograph for obtaining an effluent gas flow continuing for the period of time required for the vaporization of the compound,
   energizing said torch sufficiently to produce a thermal region capable of degrading the compound into its atomic elements,
   exposing said continuous effluent flow to said region to produce said atomization and to excite each of said atomic elements into radiation emission at its characteristic wavelength, said emissions each having an emission intensity responsive to the unit weight of the element independently of the physical structure of the compound,
   continuously with said exposure scanning a selected plurality of said wavelengths for producing outputs proportional to the emission intensities, said selection being with regard both to their intensity and their relative freedom from spectral interference, and
   utilizing the retention time in said chromatograph to determine the molecular formula of said compound according to the relationship $n = k \log T_r$, where n is the approximate carbon number, k is an experimental constant and $T_r$ is the elution period of the compound from the chromatograph.

2. The method of claim 1 wherein said molecular compounds are a plurality of organic compounds.

3. The method of claim 2 wherein said processing provides both qualitative and quantitative data defining the composition of the compound.

* * * * *